(12) United States Patent
Feinstein

(10) Patent No.: US 10,363,414 B1
(45) Date of Patent: Jul. 30, 2019

(54) COMBINED BLADDER SCANNER AND (FUNCTIONAL) INTERFERENTIAL ELECTRICAL STIMULATION DEVICE

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 15/951,318

(22) Filed: Apr. 12, 2018

(51) Int. Cl.
*A61N 1/36* (2006.01)
*A61N 1/04* (2006.01)
*A61B 5/20* (2006.01)
*A61B 8/08* (2006.01)

(52) U.S. Cl.
CPC ....... *A61N 1/36007* (2013.01); *A61N 1/0456* (2013.01); *A61N 1/36139* (2013.01); *A61B 5/204* (2013.01); *A61B 8/08* (2013.01)

(58) Field of Classification Search
CPC ............. A61N 1/36007; A61N 1/0456; A61N 1/36139; A61B 5/204; A61B 8/08
See application file for complete search history.

(56) References Cited

U.S. PATENT DOCUMENTS

| | | |
|---|---|---|
| 4,537,195 A | 8/1985 | McDonnell |
| 5,833,595 A | 11/1998 | Lin |
| 6,911,912 B2 | 6/2005 | Roe |
| 9,174,045 B2 | 11/2015 | Simon et al. |
| 9,878,154 B2 | 1/2018 | Tai |
| 2009/0254144 A1 | 10/2009 | Bhadra et al. |
| 2009/0306460 A1* | 12/2009 | Stephens ............ A61N 1/36007 600/30 |
| 2013/0310706 A1* | 11/2013 | Stone ..................... A61B 5/202 600/561 |
| 2015/0290450 A1 | 10/2015 | Kolb et al. |
| 2015/0297139 A1 | 10/2015 | Toth |
| 2016/0045731 A1 | 2/2016 | Simon et al. |
| 2017/0304614 A1* | 10/2017 | Yoo .................... A61N 1/36107 |
| 2017/0326351 A1 | 11/2017 | Schepis et al. |
| 2017/0361091 A1 | 12/2017 | Tai |

FOREIGN PATENT DOCUMENTS

| WO | WO2016134270 | 8/2016 |
|---|---|---|
| WO | WO2017132067 | 8/2017 |

* cited by examiner

*Primary Examiner* — George Manuel
(74) *Attorney, Agent, or Firm* — Forge IP, PLLC

(57) ABSTRACT

A device for assisting a patient suffering from a condition that inhibits the patient from achieving spontaneous and controlled micturition includes a controller, a stimulation power supply, a sensor providing sensor feedback indicative of a level of fullness of a bladder of the patient and a plurality of electrodes. The electrodes are disposed on an epidermis of the patient and are arranged to supply transcutaneous electrical impulses that cause contraction of the bladder and relaxation of a urinary sphincter of the patient when supplied power by the stimulation power supply. The controller causes the stimulation power supply to supply power to the plurality of electrodes in response to a determination being made that the level of fullness of the bladder has exceeded a threshold level, thereby causing the plurality of electrodes to supply the transcutaneous electrical impulses in order to trigger micturition.

26 Claims, 6 Drawing Sheets

COMBINED BLADDER SCANNER AND (FUNCTIONAL) INTERFERENTIAL ELECTRICAL STIMULATION DEVICE

FIELD OF THE INVENTION

In a broad sense, the present invention relates to a system which combines a diagnostic device that evaluates the level of fulness of some liquid (or other material) containing structure within the human or animal body, along with an electrical stimulation device for stimulating a sphincter or the like associated with the liquid/material containing structure. In a more specific sense, the present invention relates to a bladder scanner device (such as, but not limited to, an ultrasound scanner) combined with an electrical stimulator, such as an Interferential Current (IFC) device, or other type of deep penetration electrical stimulation that is non-invasive and external (i.e., transcutaneous), which device may be used, for example, to eliminate the need for a straight-cath or indwelling urinary catheter in the recovery room or post anesthesia following a surgery or other medical procedure, or in patients with spinal cord injury or suffering from any type of neurogenic or atonic bladder pathology, urinary incontinence or any other voiding dysfunction of the genitourinary system.

BACKGROUND OF THE INVENTION

For more than 3500 years, urinary catheters have been used to drain the bladder when it fails to empty. For people with impaired bladder function and for whom the method is feasible, clean intermittent self-catheterization is the optimal procedure. For those who require an indwelling catheter, whether short- or long-term, the self-retaining Foley catheter is invariably used, as it has been since its introduction nearly 80 years ago, despite the fact that this catheter can cause bacterial colonization, recurrent and chronic infections, bladder stones and septicemia, damage to the kidneys, the bladder and the urethra, and contribute to the development of antibiotic resistance. In terms of medical, social and economic resources, the burden of urinary retention and incontinence, aggravated by the use of the Foley catheter, is huge. Therefore, there is an urgent need for the development of an alternative to the indwelling catheter system.

Post-Operative Urinary Retention ("POUR") syndrome resulting from anesthesia, and urinary retention from other causes (atonic bladder, spinal cord injury, etc.) requires transurethral bladder catheterization. The catheterization required can be intermittent (single or repetitive straight caths) until the anesthetic wears off over time, or patient ambulation and activity restores normal muscular and postural feedback mechanisms for urination. Alternatively an indwelling/longer term catheter may be required for situations that require more than several hours to return to normal mechanisms or are permanent in nature. The risks and complications known to accompany urinary catheterization are many and can be mild or life threatening. The longer the catheter is in place the greater the likelihood of complication, particularly urinary tract infection ("UTI")

Bladder catheterization is also a commonly used procedure during inpatient or outpatient major or minor surgery to facilitate monitoring of critical vital signs and data such as urine output, intravenous fluid and volume replacement needs during the perioperative and intraoperative periods. Monitoring urine output, (requiring catheterization) often serves as a surrogate marker of hemodynamic stability. The increase in outpatient and fast-track surgical procedures, makes it much more difficult to obtain this vital monitoring data due to the associated shortened time frames for available intraoperative and postoperative observation prior to home discharge. Holding the patient in the hospital setting because of failure to void spontaneously for whatever reason is an economic issue causing increased global healthcare system costs. It has become one of a number of first line quality of care criteria being used to establish re-imbursement penalties and organizational performance and quality ratings. This issue, combined with catheter associated complications, makes providers reluctant to catheterize patients, despite the fact that the data obtained is still required to monitor the patient's safety and recovery. Urethral catheterization is restricted to fewer procedures and for a much shortened period of time. There currently are no alternatives to catheterization that are safe and provide the combination of monitoring bladder volume together with a way to cause bladder voiding non-invasively (i.e., without catheterization).

The present invention solves these problems by eliminating the need for catherization.

Urinary incontinence (UI) is a second extremely common genitourinary system problem in search of a simple, non-invasive solution. Although standard treatment for UI does not involve catheterization, the problems with abnormal muscular function and neurologic control causing the symptoms can be alleviated by the invention described herein.

The bladder is composed of a body formed by the detrusor muscle and a funnel-shaped neck. The neck has an internal layer of smooth muscle that surrounds the internal meatus of the bladder—the internal urethral sphincter. The external urethral sphincter is formed collectively by the overlying striated muscle fibers of the pelvic floor. The adult urinary bladder has a capacity of 400 to 600 ml. The bladder is innervated by efferent somatic, sympathetic, and parasympathetic fibers, whereas the visceral afferent fibers arise from the bladder wall (stretch receptors).

The parasympathetic fibers cause contraction of the detrusor and relaxation of the neck, permitting micturition. The sympathetic fibers, in contrast, influence the relaxation of the detrusor and close the internal urethral sphincter. These two systems are governed by spinal reflexes, which are regulated by two pontine brainstem centers, the pontine storage center and the pontine micturition center. The voluntary control of the bladder becomes fully developed by the first few years of life and involves the coordination among the frontal cortex, the pontine centers, and the spinal segments influencing bladder control. During micturition, two phases can be distinguished, the storage phase and the emptying phase.

The highly compliant bladder allows for storage of a large volume of urine without an increase in the intravesical pressure. The first urge to void is felt at a bladder volume of 150 ml. The tension receptors in the bladder wall are activated at a volume of approximately 300 ml, creating the sense of fullness. The activation of the tension receptors propagates signals that travel through the pelvic sensory nerves, arriving at the spinal cord, where they activate parasympathetic neurons. Activation of the parasympathetic neuron stimulates efferent pelvic nerves that lead to contraction of the detrusor muscle. Detrusor contractions last only a few seconds, substantially raising the intravesical pressure from a resting pressure of 40 mm $H_2O$ to a few hundred mm $H_2O$. When the intravesical pressure reaches the voiding threshold, the detrusor contractions increase in intensity, frequency, and duration. This creates a complete and synchronous contraction of the detrusor muscle, allowing the bladder to empty quickly and efficiently.

If micturition is not desired or is inconvenient, afferent stimuli from the stretch receptors of the bladder along with the proprioceptive afferents of the urethra, penis, vagina, rectum perineum, and anal sphincters activate the sympathetic system and external urethral sphincter motor neurons and simultaneously inhibit the parasympathetic system. The final effect is to prevent micturition through the contraction of the sphincters and the relaxation of detrusor muscle. Furthermore cerebral input from the frontal cortex and the pontine centers also aids in inhibiting the parasympathetic neurons and activating the sympathetic pathways.

During, and shortly after, medical and surgical procedures, however, particularly those involving the use of general or spinal anesthesia, the above-described micturition process may be disrupted in a variety of ways. Traditionally, bladder catheterization has been employed during, and shortly after, medical and surgical procedures to address this issue. However, given today's increase in outpatient and fast-track surgical procedures, simpler and less invasive alternatives would be desirable.

Additionally, spinal cord injuries and other paralytic conditions may result in an atonic bladder or denervated voiding conditions. Moreover, UI also results from similar bladder and sphincter pathology, despite having no relationship to anesthesia or issues noted above related to need for catheterization.

Previously, attempts have been made to apply electrical stimulation to control the bladder and bowel. These previous attempts have predominantly focused on activation of the detrusor by sacral root, sacral plexus, or peripheral nerve stimulation, activating either motor or sensory nerves using various types of electrodes, such as cuff electrodes, subcutaneous electrodes, spiral electrodes, needle probes, dermal surface electrodes or surface mounted needles, and surgically implanted stimulators, to apply an electrical stimulus that may take the form of a pulse burst electrical stimulation or a continuous stimulation. Problems exist with these known types of therapies. The stimulation modalities used, in order to generate the requisite low frequency impulses required to achieve desirable results, may cause the patient to suffer pain, discomfort and/or tissue damage in the areas of electrical stimulation application and/or require invasive procedures to install the devices used. Also, they cannot accurately target deeper internal structures without such an invasive type surgical procedure.

Therefore, what is desired is a system and method for assisting with micturition in a patient with an anesthetized bladder, or suffering from spinal cord injuries and/or other paralytic conditions resulting in an atonic bladder or denervated voiding conditions, certain types of lower urinary tract obstructions, and pelvic floor muscle dysfunction as seen in urinary incontinence, which avoids the problems and medical complications associated with known systems and methods, already described, particularly the use of intermittent or indwelling catheterization, and also for simple ongoing control of urinary incontinence problems that may or may not require such catheter instrumentation.

SUMMARY OF THE INVENTION

In general terms, the present invention is directed to a bladder scanner (e.g., ultrasound) combined with an electrical stimulator—interferential current (IFC) technology or other type of deep penetration electrical stimulation that is non-invasive and external (i.e. transcutaneous)—of the bladder to eliminate the need for a straight-cath or indwelling urinary catheter. The combined device would cause an anesthetized or abnormally functioning bladder and urinary system to contract and the urinary sphincter to relax—two independent but synchronously timed events involving two separate anatomic structures, and therefore, two separate stimuli appropriately timed—in response to scanner monitoring that indicates the bladder is over filled with urine while the spinal or general anesthesia is wearing off. After such stimulation the bladder and urinary sphincter (and if a clinical problem, the pelvic floor muscles—external sphincter) regain their normal muscular contractile powers for spontaneous and controlled voiding.

The device could also be used in spinal cord injuries and other paralytic conditions that result in an atonic bladder or denervated voiding condition, urinary incontinence problems, and in certain cases of lower urinary tract obstructions.

The preferred embodiment presented as an example here illustrates that the frequencies of the crossover/merged/waveform currents generated by the IFC device would be designed so that one set of currents may have a sympathetic nerve stimulation property for bladder muscle contraction and the other set of overlapping currents has a parasympathetic nerve stimulation property for sphincter relaxation.

A specific exemplary embodiment of such a device for assisting a patient suffering from a condition that inhibits the patient from achieving spontaneous and controlled micturition comprises a controller, a stimulation power supply in communication with the controller, a sensor providing sensor feedback to the controller, the sensor feedback indicative of a level of fullness of a bladder of the patient and a plurality of electrodes in electrical communication with the stimulation power supply, the plurality of electrodes disposed on an epidermis of the patient and arranged to supply transcutaneous electrical impulses that cause contraction of the bladder and relaxation of a urinary sphincter of the patient when supplied power by the stimulation power supply. The controller causes the stimulation power supply to supply power to the plurality of electrodes in response to a determination being made that the level of fullness of the bladder has exceeded a threshold level, thereby causing the plurality of electrodes to supply the transcutaneous electrical impulses in order to trigger micturition.

In some embodiments, the sensor comprises an ultrasound sensor. In some embodiments, the stimulation power supply comprises an interferential therapy power supply, and the plurality of electrodes comprises at least two electrodes supplying transcutaneous electrical impulses at two different frequencies, the transcutaneous electrical impulses provided at two different frequencies giving rise to at least one beat impulse having an interference frequency.

In certain embodiments, the plurality of electrodes comprises a first pair of electrodes supplying transcutaneous electrical impulses at a first frequency and a second pair of electrodes supplying transcutaneous electrical impulses at a second frequency different than the first frequency, the transcutaneous electrical impulses provided at the first and second frequencies giving rise to a beat impulse having an interference frequency. In certain of these embodiments, the beat impulse has a sympathetic nerve stimulation property to stimulate bladder contraction, a parasympathetic nerve stimulation property to stimulate internal urinary sphincter relaxation and/or a somatic nerve stimulation property to stimulate external urinary sphincter relaxation.

In certain embodiments, the plurality of electrodes comprises: a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency. The plurality of electrodes further comprises a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency. In certain of these embodiments, the first beat impulse has a sympathetic nerve stimulation property to stimulate bladder contraction and the second beat impulse has a parasympathetic nerve stimulation property to stimulate urinary sphincter relaxation.

In certain embodiments, the plurality of electrodes further comprises: a fifth electrode supplying transcutaneous electrical impulses at a fifth frequency and a sixth electrode supplying transcutaneous electrical impulses at a sixth frequency different than the fifth frequency, the transcutaneous electrical impulses provided at the fifth and sixth frequencies giving rise to a third beat impulse having a third interference frequency. In some of these embodiments, the third beat impulse has a somatic nerve stimulation property to stimulate external urinary sphincter relaxation.

In certain embodiments, the plurality of electrodes comprises a first pair of electrodes supplying transcutaneous electrical impulses at a first frequency and a second pair of electrodes supplying transcutaneous electrical impulses at a second frequency different than the first frequency, the transcutaneous electrical impulses provided at the first and second frequencies giving rise to a first beat impulse having a first interference frequency. The plurality of electrodes further comprises a third pair of electrodes supplying transcutaneous electrical impulses at a third frequency and a fourth pair of electrodes supplying transcutaneous electrical impulses at a fourth frequency different than the third frequency, the transcutaneous electrical impulses provided at the third and fourth frequencies giving rise to a second beat impulse having a second interference frequency. In certain of these embodiments, the first beat impulse has a sympathetic nerve stimulation property to stimulate bladder contraction and the second beat impulse has a parasympathetic nerve stimulation property to stimulate urinary sphincter relaxation.

In some embodiments, the condition that inhibits the patient from achieving spontaneous and controlled micturition is an anesthetized bladder. In other embodiments, the condition that inhibits the patient from achieving spontaneous and controlled micturition is a spinal cord injury or other paralytic condition that results in an atonic bladder or denervated voiding condition.

In accordance with another exemplary embodiment of the present invention, a device for assisting a patient suffering from a condition that inhibits the patient from achieving spontaneous and controlled micturition, comprises a controller, an interferential therapy power supply in communication with the controller, an ultrasound sensor providing sensor feedback to the controller, the sensor feedback indicative of a level of fullness of a bladder of the patient, and a plurality of electrodes in electrical communication with the interferential therapy power supply, the plurality of electrodes disposed on an epidermis of the patient and arranged to supply transcutaneous electrical impulses that cause contraction of the bladder and relaxation of a urinary sphincter of the patient when supplied power by the interferential therapy power supply. The plurality of electrodes comprises a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency. The plurality of electrodes further comprise a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency. The controller causes the interferential therapy power supply to supply power to the plurality of electrodes in response to a determination being made that the level of fullness of the bladder has exceeded a threshold level, thereby causing the plurality of electrodes to supply the transcutaneous electrical impulses in order to trigger micturition.

In some embodiments, the first beat impulse has a sympathetic nerve stimulation property to stimulate bladder contraction and the second beat impulse has a parasympathetic nerve stimulation property to stimulate urinary sphincter relaxation.

In some embodiments, the condition that inhibits the patient from achieving spontaneous and controlled micturition is an anesthetized bladder. In other embodiments, the condition that inhibits the patient from achieving spontaneous and controlled micturition is a spinal cord injury or other paralytic condition that results in an atonic bladder or denervated voiding condition.

In another aspect of the present invention, a method for assisting a patient suffering from a condition that inhibits the patient from achieving spontaneous and controlled micturition comprises the steps of: (a) sensing a level of fullness of a bladder of the patient using an ultrasound sensor; and (b) in response to a determination being made that the level of fullness of the bladder has exceeded a threshold level, performing the following steps: (i) supplying transcutaneous electrical impulses at a first frequency and supplying transcutaneous electrical impulses at a second frequency different than the first frequency, the transcutaneous electrical impulses provided at the first and second frequencies giving rise to a first beat impulse having a first interference frequency; and (ii) supplying transcutaneous electrical impulses at a third frequency and supplying transcutaneous electrical impulses at a fourth frequency different than the third frequency, the transcutaneous electrical impulses provided at the third and fourth frequencies giving rise to a second beat impulse having a second interference frequency.

In some embodiments, the first beat impulse has a sympathetic nerve stimulation property to stimulate bladder contraction and the second beat impulse has a parasympathetic nerve stimulation property to stimulate urinary sphincter relaxation.

In some embodiments, the method further comprises the step of supplying transcutaneous electrical impulses at a fifth frequency and supplying transcutaneous electrical impulses at a sixth frequency different than the fifth frequency, the transcutaneous electrical impulses provided at the fifth and sixth frequencies giving rise to a third beat impulse having a third interference frequency. In certain of these embodiments, the first beat impulse has a sympathetic nerve stimulation property to stimulate bladder contraction, the second beat impulse has a parasympathetic nerve stimulation property to stimulate urinary sphincter relaxation and the third beat impulse has a somatic nerve stimulation property to stimulate external urinary sphincter relaxation.

In some embodiments, the condition that inhibits the patient from achieving spontaneous and controlled micturition is an anesthetized bladder. In other embodiments, the condition that inhibits the patient from achieving spontaneous and controlled micturition is a spinal cord injury or other paralytic condition that results in an atonic bladder or denervated voiding condition.

The embodiments as discussed above are illustrative and are not intended to exhaust all possible arrangements, modifications, and variations of features of the invention.

DETAILED DESCRIPTION OF THE INVENTION

As used herein, the terms "electrode" and electrodes" encompass electrical coils, electrical plates, electrical conductors, conductive fabrics and gels, and any other conductive materials and devices.

Figure 1:
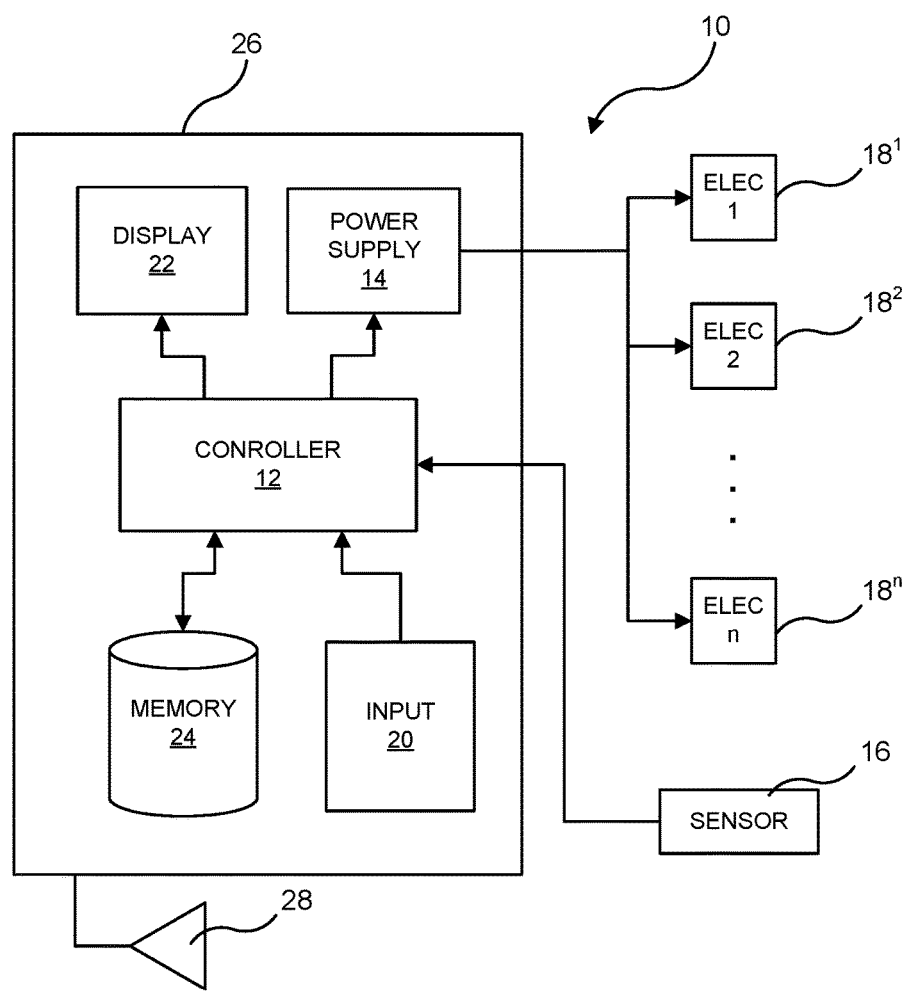
FIG. 1 is a block diagram illustrating a device for assisting a patient suffering from a condition that inhibits the patient from achieving spontaneous and controlled micturition according to an exemplary embodiment of the present invention.

Referring to the figures in detail and first to FIG. 1, there is shown an exemplary embodiment of a device (10) for assisting a patient (50) suffering from a condition that inhibits the patient (50) from achieving spontaneous and controlled micturition. The device (10) includes a controller (12), a stimulation power supply (14) in communication with the controller (12) and a sensor (16) providing sensor feedback to the controller (12), the sensor feedback indicative of a level of fullness of a bladder of the patient (50). The device (10) also includes a plurality of electrodes ($18^1$, $18^2$ ... $18n$) in electrical communication with the stimulation power supply (14).

The plurality of electrodes ($18^1$, $18^2$ ... $18n$) are disposed on an epidermis (52) of the patient (50) and are arranged to supply transcutaneous electrical impulses that cause contraction of the bladder and relaxation of a urinary sphincter of the patient when supplied power by the stimulation power supply. Various options are possible for electrode ($18^1$, $18^2$ ... $18n$) placement, as is explained in more detail below. The sensor (16) may comprise, for example, an ultrasound sensor.

The controller (12) causes the stimulation power supply (14) to supply power to the plurality of electrodes ($18^1$, $18^2$ ... $18n$) in response to a determination being made by the controller (12), at least in part based on the sensor feedback received from the sensor (16), that the level of fullness of the bladder has exceeded a threshold level. As is explained in more detail below, the power supplied to the plurality of electrodes ($18^1$, $18^2$ ... $18n$) is such that transcutaneous electrical impulses are created in order to trigger micturition.

The device (10) also includes an input mechanism (20), such as a keyboard, joystick or the like as is known in the art, which allows the user to enter control parameters and the like. As but one example, input mechanism (20) may include a button or other type of controller to turn the device on or off manually, or to trigger micturition. This may be particularly desirable, for example, when the device is used in connection with urinary incontinence.

Also as is well known in the art, the device (10) includes a display (22) to provide visual and/or auditory output to a user of the device (10). The display (22) may also present the user with other helpful information. For example, the device (10) may be linked to a mapping app on a mobile device (such as Google maps or Waze) in order to display or otherwise provide information concerning appropriate bathroom facilities when in public.

The device may further include an antenna (28) or the like (such as Bluetooth functionality) in order to provide connectivity to a mobile network or direct connectivity to a mobile phone, computerized fitness tracker, smart watch, etc. The antenna (28) or the like may also be used to provide wireless connectivity for the sensor (16) rather than employing a wired connection.

The device (10) further includes a memory (24), which allows the device to store various parameters that may be employed by the controller (12), such as the aforementioned threshold level of fullness of the bladder.

The controller (12), stimulation power supply (14), input mechanism (20), display (22), memory (24) and antenna (28) may be contained in a housing (26), as should be apparent to those skilled in the art. Various types of connectors may be provided on the housing to allow for connection of the electrodes ($18^1$, $18^2$ ... $18n$), the sensor (16), or various other devices (e.g., mobile phones, tablets, smart watches, etc.) also as should be apparent to those skilled in the art.

Although use of various types of deep penetration electrical stimulation that is non-invasive and external (i.e. transcutaneous) is contemplated, the presently discussed exemplary embodiment employs interferential current (IFC) technology.

In general, IFC therapy utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current was at 4000 Hz and the other current at 3900 Hz, the resultant beat frequency would be at 100 Hz.

Thus, the basic principle of IFC therapy is to utilize the strong physiological effects of the low frequency electrical stimulation of muscle and nerve tissues at sufficient depth, without the associated painful and somewhat unpleasant side effects of such stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current.

In other words, the lower the stimulation frequency, the greater the resistance to the passage of the current, so more discomfort is experienced. The skin impedance at 50 Hz is approximately 3200 ohms, whilst at 4000 Hz it is reduced to approximately 40 ohms. The result of applying this latter frequency is that it will pass more easily through the skin and any other tissues before hitting the target tissue or organ with a therapeutic beat frequency resulting in the desired physiologic response from the target organ or tissue, requiring less electrical energy input to the deeper tissues, giving rise to less discomfort.

Figure 2:
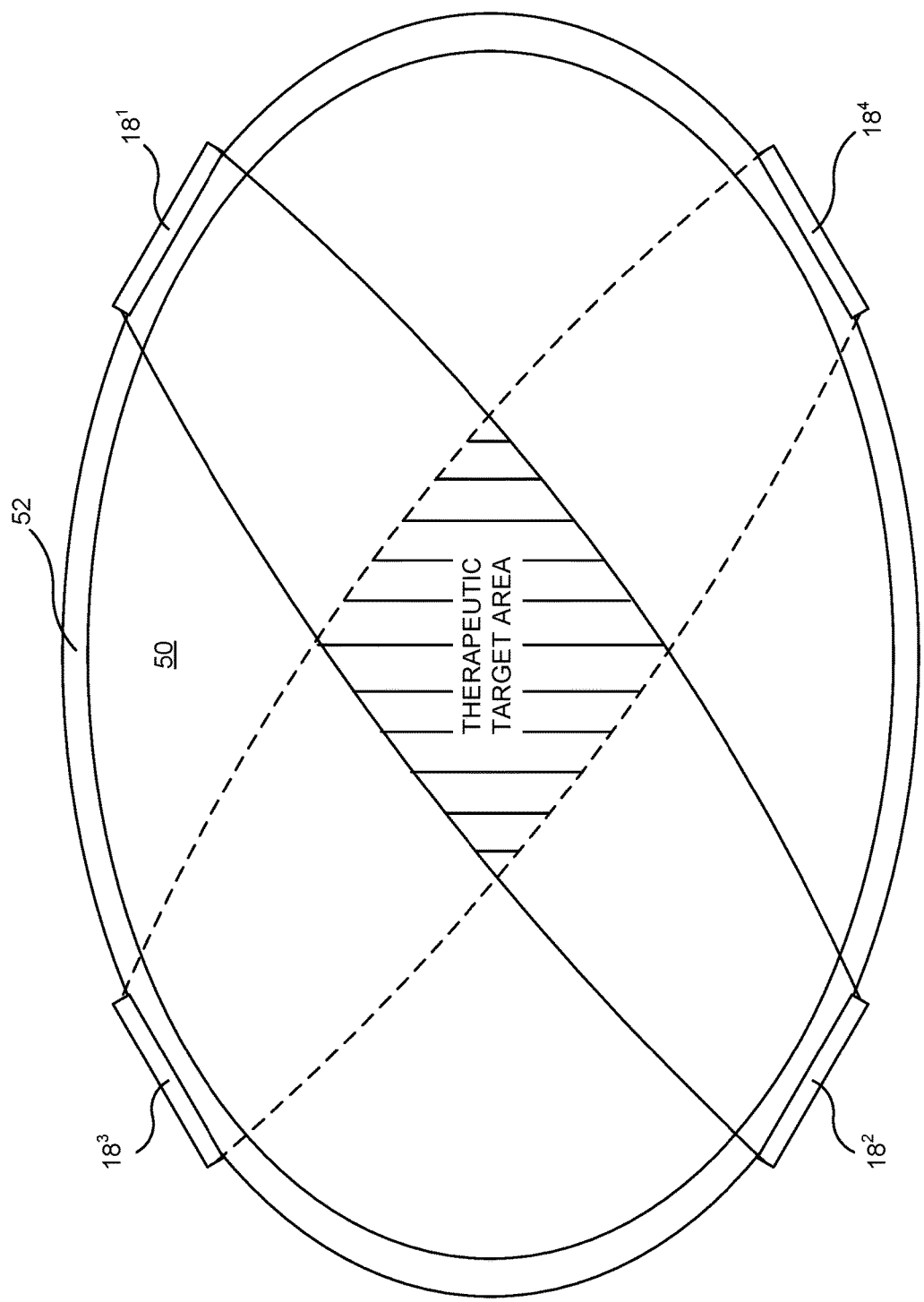
FIG. 2 is schematic view illustrating operational characteristics of the device shown in FIG. 1.

Referring now to FIG. 2, an exemplary arrangement of electrodes employing IFC therapy is shown applied to the epidermis (52) of a patient (50). In this example, a first pair of electrodes ($18^1$, $18^2$) supplies transcutaneous electrical impulses at a first frequency (represented by solid lines) and a second pair of electrodes ($18^3$, $18^4$) supplies transcutaneous electrical impulses at a second frequency (represented by dashed lines) different than the first frequency. The transcutaneous electrical impulses provided at the first and second frequencies giving rise to a beat impulse in a Therapeutic Target Area (located at the position shown in FIG. 2 where the area defined by solid lines and the area defined by dashed lines overlap) having an interference frequency. The beat impulse has a sympathetic nerve stimulation property to stimulate bladder contraction and/or a parasympathetic nerve stimulation property to stimulate internal urinary sphincter relaxation and/or a somatic nerve stimulation property to stimulate nerves of the pelvic floor (i.e., external urinary sphincter).

For example, it has been found that beat impulses having a frequency in the range of from 1-5 Hz may provide desirable stimulation properties for the sympathetic nerves in question, beat impulses having a frequency in the range of from 10-150 Hz may provide desirable stimulation properties for the parasympathetic nerves in question and beat impulses having a frequency in the range of from 10-50 Hz may provide desirable stimulation properties for the pelvic floor somatic nerves in question.

Figure 3:
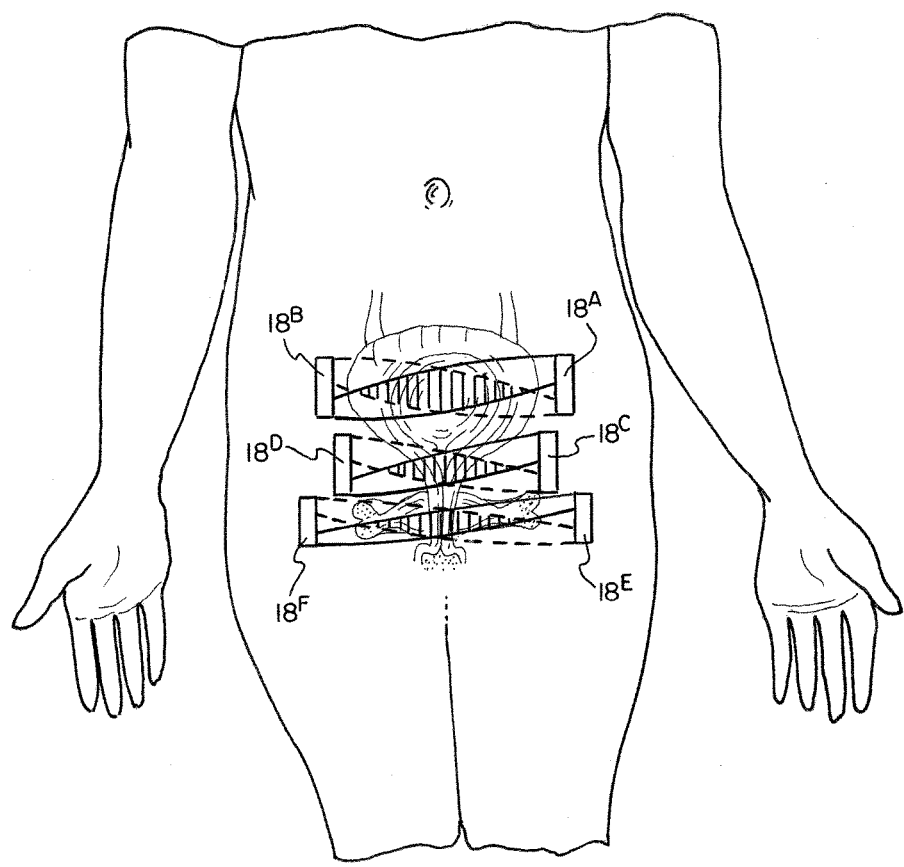
FIG. 3 is schematic view illustrating the device shown in FIG. 1 being used on a patient.

Turning now to FIG. 3, an exemplary positioning of the electrodes ($18^A$-$18^F$) on the patient (50) is shown. In this exemplary embodiment, a first electrode ($18^A$) supplies transcutaneous electrical impulses at a first frequency and a second electrode ($18^B$) supplies transcutaneous electrical impulses at a second frequency different than the first frequency, the transcutaneous electrical impulses provided at the first and second frequencies giving rise to a first beat impulse having a first interference frequency. The first and second electrodes ($18^A$, $18^B$) are positioned such the Therapeutic Target Area thereof (shown with vertical cross-hatching) is positioned to cause sympathetic nerve stimulation of the bladder. As mentioned previously, the first beat impulse may desirably have a frequency falling within the range of from 1-5 Hz.

A third electrode ($18^C$) supplies transcutaneous electrical impulses at a third frequency and a fourth electrode ($18^D$) supplies transcutaneous electrical impulses at a fourth frequency different than the third frequency, the transcutaneous electrical impulses provided at the third and fourth frequencies giving rise to a second beat impulse having a second interference frequency. The third and fourth electrodes ($18^C$, $18^D$) are positioned such the Therapeutic Target Area thereof (shown with vertical cross-hatching) is positioned to cause parasympathetic nerve stimulation of the internal urinary sphincter. As mentioned previously, the second beat impulse may desirably have a frequency falling within the range of from 10-150 Hz.

A fifth electrode ($18^E$) supplies transcutaneous electrical impulses at a fifth frequency and a sixth electrode ($18^F$) supplies transcutaneous electrical impulses at a sixth frequency different than the fifth frequency, the transcutaneous electrical impulses provided at the fifth and sixth frequencies giving rise to a third beat impulse having a third interference frequency. The fifth and sixth electrodes ($18^E$, $18^F$) are positioned such the Therapeutic Target Area thereof (shown with vertical cross-hatching) is positioned to cause somatic nerve stimulation of the pelvic floor (i.e., external urinary sphincter). As mentioned previously, the third beat impulse may desirably have a frequency falling within the range of from 10-50 Hz.

Figure 4A:
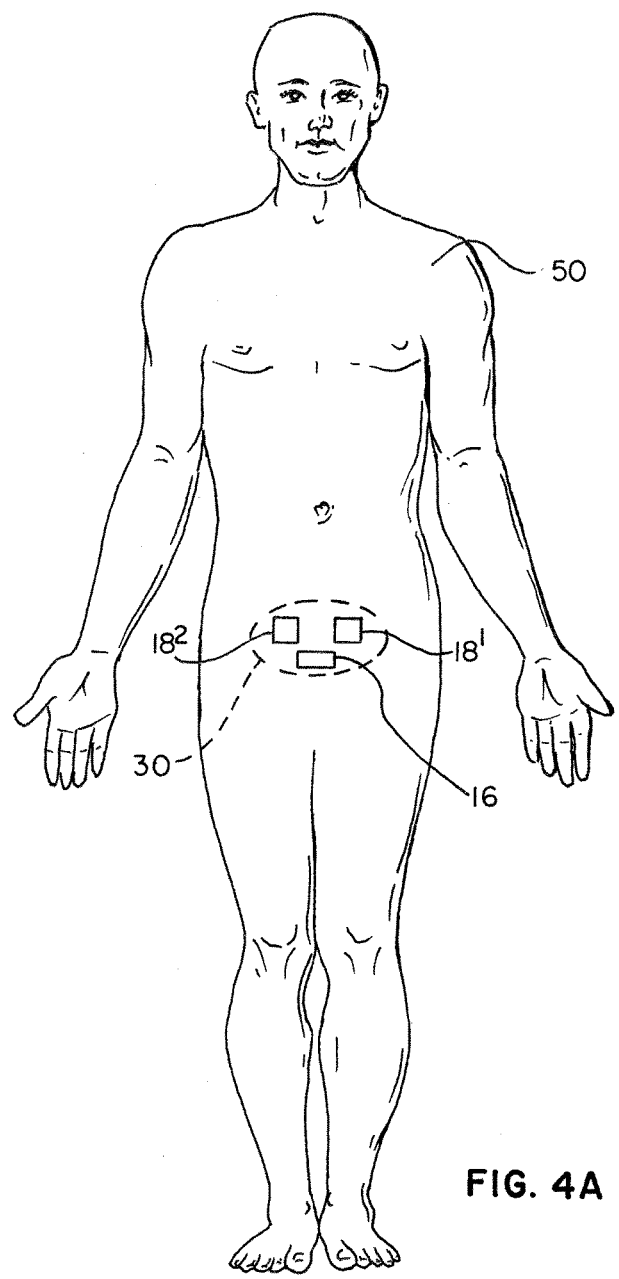
FIGS. 4A-4C are schematic views illustrating various exemplary options for the placement on a patient of the electrodes of the device shown in FIG. 1.
Figure 4B:
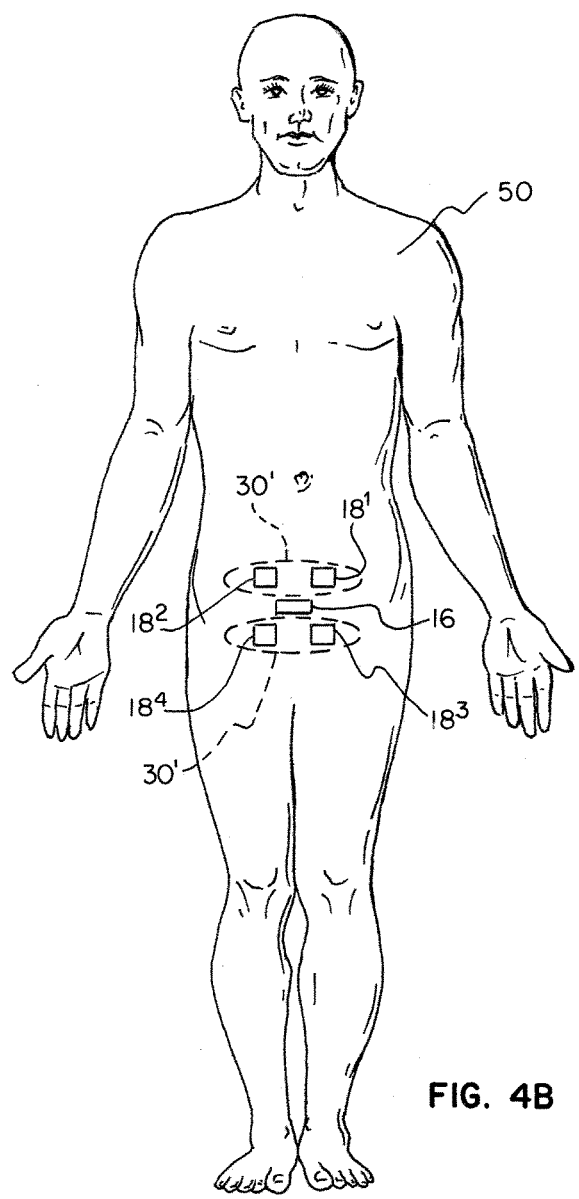
Figure 4C:
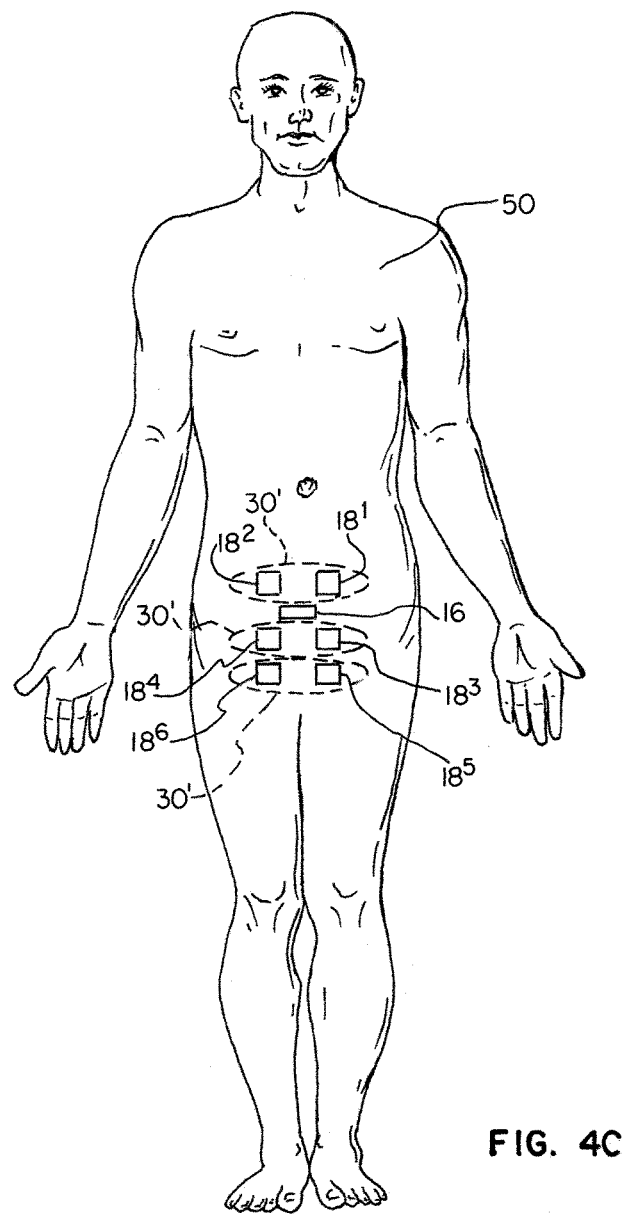

Referring now to FIGS. 4A-4C, other exemplary arrangements of electrodes employing IFC therapy is shown, as is the placement of the sensor (16) on the patient (50).

In the exemplary embodiment of FIG. 4A, a first pair of electrodes ($18^1$, $18^2$) is positioned similarly to first and second electrodes ($18^A$, $18^B$) of FIG. 3, for example to cause sympathetic nerve stimulation of the bladder. Also shown in FIG. 4A is sensor (16) positioned on the patient (50).

Each of the first pair of electrodes ($18^1$, $18^2$) may be formed as a separate pad, or as illustrated in FIG. 4A, both electrodes ($18^1$, $18^2$) may be disposed on a common pad (30) for ease of placement on the patient (50). In the example of FIG. 4A, the sensor (16) is also disposed on the same pad (30) for further ease of placement.

In the exemplary embodiment of FIG. 4B, a first pair of electrodes ($18^1$, $18^2$) is positioned similarly to first and second electrodes ($18^A$, $18^B$) of FIG. 3, for example to cause sympathetic nerve stimulation of the bladder. Additionally, a second pair of electrodes ($18^3$, $18^4$) is positioned similarly to third and fourth electrodes)($18^C$, $18^D$) of FIG. 3, for example to cause parasympathetic nerve stimulation of the internal urinary sphincter. Again shown in FIG. 4B is sensor (16) positioned on the patient (50).

Similar to FIG. 4A, both of the first pair of electrodes ($18^1$, $18^2$) are disposed on a common pad (30') and both of the second pair of electrodes ($18^3$, $18^4$) are disposed on another common pad (30') for ease of placement on the patient (50). In the example of FIG. 4B, however, the sensor (16) is disposed separately from the electrode carrying pads (30').

The exemplary embodiment of FIG. 4C is very similar to the exemplary embodiment of FIG. 4B, with the exception that this embodiment also includes a third pair of electrodes ($18^5$, $18^6$) positioned similarly to fifth and sixth electrodes ($18^E$, $18_F$) of FIG. 3, for example to cause somatic nerve stimulation of the pelvic floor (i.e., external urinary sphincter).

The present invention therefore allows for assisting a patient suffering from an anesthetized bladder (or a spinal cord injury or other paralytic condition that results in an atonic bladder or denervated voiding condition) to achieve spontaneous and controlled micturition. The present invention also allows for assisting a patient suffering from urinary incontinence to achieve controlled micturition at a desired time and place.

Although the invention has been described with reference to particular arrangement of parts, features, and the like, these are not intended to exhaust all possible arrangements or features, and indeed many modifications and variations will be ascertainable to those of skill in the art.

The present invention is designed so that any electrical or mechanical types of deep penetration electrical stimulation that is non-invasive and external (i.e. transcutaneous) that are available but have not been incorporated into the description of the invention, or that become available as technology advances, are considered part of the invention and incorporated by modifying the electrical and mechanical parts and protocols associated with them to the achieve the aims of the present invention.

Additionally, in some embodiments configured for use in connection with situations where micturition is uncontrolled or spontaneous, as in urinary incontinence, the stimulation beats and neurologic effects are reversed as compared to the exemplary embodiment described in detail above, to relax the bladder and maintain sphincter tightness until controlled micturition is needed based on bladder fullness—either as noted by the patient's own sensory feedback mechanisms (i.e., in incontinence sensation and feeling the urge to void remain present as it is not an anesthetized or denervated state) or determined by the bladder scanner/ultrasound/sensor component of the system. Furthermore, in some situations, some of the above-described electrodes may be omitted, such as for example, with electrodes strategically placed to address only pelvic floor muscular pathology.

What is claimed is:

1. A device for assisting a patient suffering from a condition that inhibits the patient from achieving spontaneous and controlled micturition, said device comprising:
    a controller;
    a stimulation power supply in communication with said controller;
    a sensor providing sensor feedback to said controller, said sensor feedback indicative of a level of fullness of a bladder of the patient;
    a plurality of electrodes in electrical communication with said stimulation power supply, said plurality of electrodes comprising at least one electrode disposed on an epidermis of the patient and arranged to supply transcutaneous electrical impulses that cause contraction of the bladder when supplied power by said stimulation power supply and at least one electrode disposed on an epidermis of the patient and arranged to supply transcutaneous electrical impulses that cause relaxation of a urinary sphincter of the patient when supplied power by said stimulation power supply; and
    wherein said controller causes said stimulation power supply to supply power to the plurality of electrodes in response to a determination being made that the level of fullness of the bladder has exceeded a threshold level, thereby causing said plurality of electrodes to supply the transcutaneous electrical impulses in order to trigger micturition.

2. The device of claim 1 wherein said sensor comprises an ultrasound sensor.

3. The device of claim 1 wherein said stimulation power supply comprises an interferential therapy power supply, and wherein said plurality of electrodes comprises at least two electrodes supplying transcutaneous electrical impulses at two different frequencies, the transcutaneous electrical impulses provided at two different frequencies giving rise to at least one beat impulse having an interference frequency.

4. The device of claim 3 wherein said plurality of electrodes comprises a first pair of electrodes supplying transcutaneous electrical impulses at a first frequency and a second pair of electrodes supplying transcutaneous electrical impulses at a second frequency different than the first frequency, the transcutaneous electrical impulses provided at the first and second frequencies giving rise to a beat impulse having an interference frequency.

5. The device of claim 4 wherein said beat impulse has a sympathetic nerve stimulation property to stimulate bladder contraction, a parasympathetic nerve stimulation property to stimulate internal urinary sphincter relaxation and/or a somatic nerve stimulation property to stimulate external urinary sphincter relaxation.

6. The device of claim 3 wherein said plurality of electrodes comprises:
    a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency; and
    a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency.

7. The device of claim 6 wherein said first beat impulse has a sympathetic nerve stimulation property to stimulate bladder contraction and the second beat impulse has a parasympathetic nerve stimulation property to stimulate internal urinary sphincter relaxation.

8. The device of claim 6 wherein said plurality of electrodes further comprises:
    a fifth electrode supplying transcutaneous electrical impulses at a fifth frequency and a sixth electrode supplying transcutaneous electrical impulses at a sixth frequency different than the fifth frequency, the transcutaneous electrical impulses provided at the fifth and sixth frequencies giving rise to a third beat impulse having a third interference frequency.

9. The device of claim 8 wherein said first beat impulse has a sympathetic nerve stimulation property to stimulate bladder contraction, the second beat impulse has a parasympathetic nerve stimulation property to stimulate urinary sphincter relaxation and the third beat impulse has a somatic nerve stimulation property to stimulate external urinary sphincter relaxation.

10. The device of claim 3 wherein said plurality of electrodes comprises:
    a first pair of electrodes supplying transcutaneous electrical impulses at a first frequency and a second pair of electrodes supplying transcutaneous electrical impulses at a second frequency different than the first frequency, the transcutaneous electrical impulses provided at the first and second frequencies giving rise to a first beat impulse having a first interference frequency; and
    a third pair of electrodes supplying transcutaneous electrical impulses at a third frequency and a fourth pair of electrodes supplying transcutaneous electrical impulses at a fourth frequency different than the third frequency, the transcutaneous electrical impulses provided at the third and fourth frequencies giving rise to a second beat impulse having a second interference frequency.

11. The device of claim 10 wherein said first beat impulse has a sympathetic nerve stimulation property to stimulate bladder contraction and the second beat impulse has a parasympathetic nerve stimulation property to stimulate urinary sphincter relaxation.

12. The device of claim 1 wherein the condition that inhibits the patient from achieving spontaneous and controlled micturition is an anesthetized bladder.

13. The device of claim 1 wherein the condition that inhibits the patient from achieving spontaneous and controlled micturition is a spinal cord injury or other paralytic condition that results in an atonic bladder or denervated voiding condition.

14. The device of claim 1 wherein the condition that inhibits the patient from achieving spontaneous and controlled micturition is urinary incontinence.

15. A device for assisting a patient suffering from a condition that inhibits the patient from achieving spontaneous and controlled micturition, said device comprising:
   a controller;
   an interferential therapy power supply in communication with said controller;
   an ultrasound sensor providing sensor feedback to said controller, said sensor feedback indicative of a level of fullness of a bladder of the patient;
   a plurality of electrodes in electrical communication with said interferential therapy power supply, said plurality of electrodes disposed on an epidermis of the patient and arranged to supply transcutaneous electrical impulses that cause contraction of the bladder and relaxation of a urinary sphincter of the patient when supplied power by said interferential therapy power supply, said plurality of electrodes comprising:
      a first electrode supplying transcutaneous electrical impulses at a first frequency and a second electrode supplying transcutaneous electrical impulses at a second frequency different than the first frequency, the transcutaneous electrical impulses provided at the first and second frequencies giving rise to a first beat impulse having a first interference frequency; and
      a third electrode supplying transcutaneous electrical impulses at a third frequency and a fourth electrode supplying transcutaneous electrical impulses at a fourth frequency different than the third frequency, the transcutaneous electrical impulses provided at the third and fourth frequencies giving rise to a second beat impulse having a second interference frequency;
   wherein said controller causes said interferential therapy power supply to supply power to the plurality of electrodes in response to a determination being made that the level of fullness of the bladder has exceeded a threshold level, thereby causing said plurality of electrodes to supply the transcutaneous electrical impulses in order to trigger micturition.

16. The device of claim 15 wherein said first beat impulse has a sympathetic nerve stimulation property to stimulate bladder contraction and the second beat impulse has a parasympathetic nerve stimulation property to stimulate urinary sphincter relaxation.

17. The device of claim 15 wherein the condition that inhibits the patient from achieving spontaneous and controlled micturition is an anesthetized bladder.

18. The device of claim 15 wherein the condition that inhibits the patient from achieving spontaneous and controlled micturition is a spinal cord injury or other paralytic condition that results in an atonic bladder or denervated voiding condition.

19. The device of claim 15 wherein the condition that inhibits the patient from achieving spontaneous and controlled micturition is urinary incontinence.

20. A method for assisting a patient suffering from a condition that inhibits the patient from achieving spontaneous and controlled micturition, said method comprising the steps of:
   sensing a level of fullness of a bladder of the patient using an ultrasound sensor;
   in response to a determination being made that the level of fullness of the bladder has exceeded a threshold level, performing the following steps:
      supplying transcutaneous electrical impulses at a first frequency and supplying transcutaneous electrical impulses at a second frequency different than the first frequency, the transcutaneous electrical impulses provided at the first and second frequencies giving rise to a first beat impulse having a first interference frequency; and
      supplying transcutaneous electrical impulses at a third frequency and supplying transcutaneous electrical impulses at a fourth frequency different than the third frequency, the transcutaneous electrical impulses provided at the third and fourth frequencies giving rise to a second beat impulse having a second interference frequency.

21. The method of claim 20 wherein the first beat impulse has a sympathetic nerve stimulation property to stimulate bladder contraction and the second beat impulse has a parasympathetic nerve stimulation property to stimulate urinary sphincter relaxation.

22. The method of claim 20 further comprising the step of supplying transcutaneous electrical impulses at a fifth frequency and supplying transcutaneous electrical impulses at a sixth frequency different than the fifth frequency, the transcutaneous electrical impulses provided at the fifth and sixth frequencies giving rise to a third beat impulse having a third interference frequency.

23. The method of claim 22 wherein the first beat impulse has a sympathetic nerve stimulation property to stimulate bladder contraction, the second beat impulse has a parasympathetic nerve stimulation property to stimulate urinary sphincter relaxation and the third beat impulse has a somatic nerve stimulation property to stimulate external urinary sphincter relaxation.

24. The device of claim 20 wherein the condition that inhibits the patient from achieving spontaneous and controlled micturition is an anesthetized bladder.

25. The device of claim 20 wherein the condition that inhibits the patient from achieving spontaneous and controlled micturition is a spinal cord injury or other paralytic condition that results in an atonic bladder or denervated voiding condition.

26. The device of claim 20 wherein the condition that inhibits the patient from achieving spontaneous and controlled micturition is urinary incontinence.

* * * * *